United States Patent

Safabash et al.

Patent Number: 5,908,054
Date of Patent: Jun. 1, 1999

[54] FLUID DISPERSION AND DELIVERY ASSEMBLY AND METHOD

[75] Inventors: Jason H. Safabash, Sherman Oaks; Christopher S. Dauer, San Francisco, both of Calif.

[73] Assignee: Fusion Medical Technologies, Inc., Mountian View, Calif.

[21] Appl. No.: 09/016,490

[22] Filed: Jan. 30, 1998

Related U.S. Application Data

[63] Continuation of application No. 08/876,269, Jun. 16, 1997.

[51] Int. Cl.$^6$ ...................................................... B01F 5/12
[52] U.S. Cl. ..................................... 141/26; 141/2; 141/9; 141/27; 141/100; 141/329; 141/383; 366/130; 366/268
[58] Field of Search ............................... 141/2, 9, 25–27, 141/100, 329, 330, 383; 366/130, 167.1, 267, 268; 604/82, 83, 85, 416

[56] References Cited

U.S. PATENT DOCUMENTS

| | | | |
|---|---|---|---|
| 2,872,867 | 3/1959 | Killinger | 141/329 |
| 2,954,769 | 10/1960 | Callahan et al. | 141/330 |
| 3,700,215 | 10/1972 | Hardman et al. | 366/268 |
| 4,046,145 | 9/1977 | Choksi | 141/27 |
| 4,469,153 | 9/1984 | Morrisette | 141/364 |
| 4,743,229 | 5/1988 | Chu | 604/82 |
| 4,834,149 | 5/1989 | Fournier et al. | 141/329 |
| 4,834,152 | 5/1989 | Howson et al. | 141/329 |
| 5,088,996 | 2/1992 | Kopfer et al. | 141/329 |
| 5,158,558 | 10/1992 | Melker et al. | 141/329 |
| 5,352,036 | 10/1994 | Haber et al. | 366/130 |
| 5,425,580 | 6/1995 | Beller | 366/131 |
| 5,454,786 | 10/1995 | Harris | 604/416 |

*Primary Examiner*—J. Casimer Jacyna
*Attorney, Agent, or Firm*—Townsend and Townsend and Crew LLP

[57] ABSTRACT

A fluid dispersion and delivery assembly (49) includes first and second syringes (28,50) containing a hemostatic solution (38) and a flowable gel material (58), fluidly coupled together by a fluid transfer assembly (2). The fluid transfer assembly includes a double Luer fitting (4) and a hollow tube (6), having openings (24,22) at its ends (16,18), reciprocally mounted within the fitting. This permits the hemostatic solution in the first syringe to be evenly dispersed into the flowable gel material within the second syringe by simply pressing the plunger (46) of the first syringe. After dispersion, the fluid transfer assembly is dismounted from the second syringe to permit combined material (62) within the second syringe to be dispensed.

29 Claims, 2 Drawing Sheets

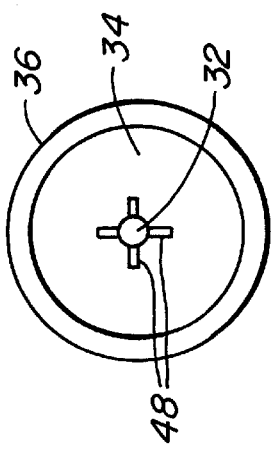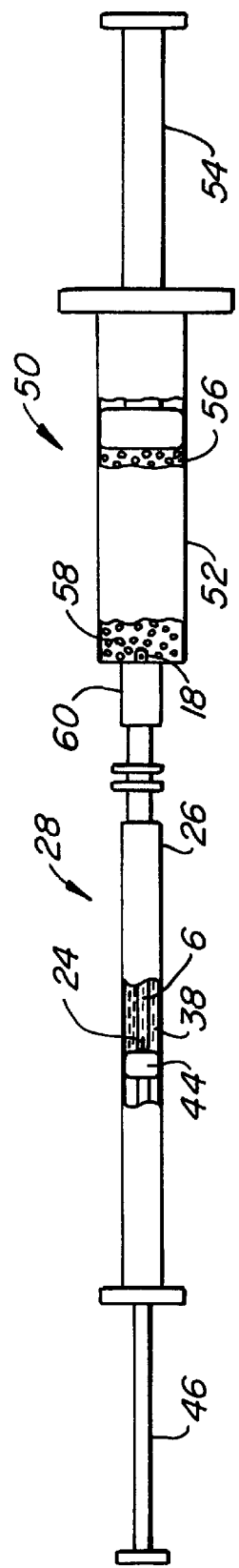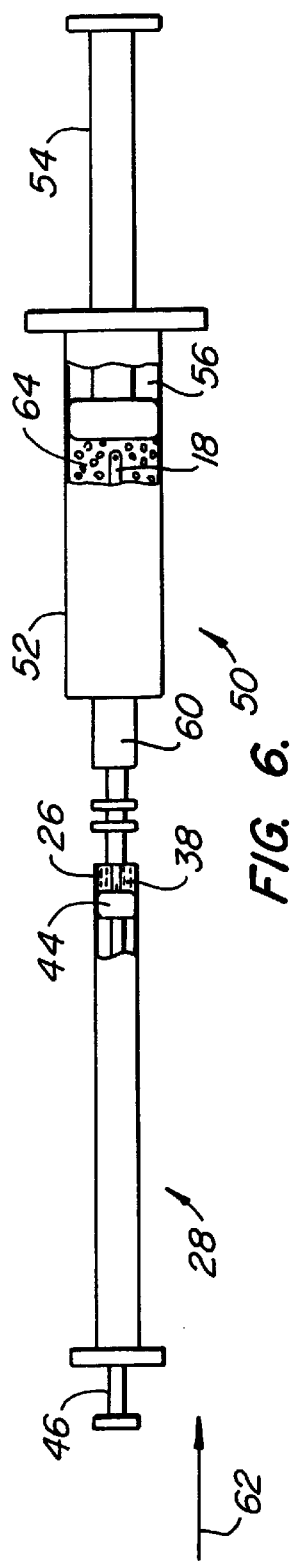

FLUID DISPERSION AND DELIVERY ASSEMBLY AND METHOD

CROSS-REFERENCE TO RELATED APPLICATION

This is a continuation of U.S. patent application Ser. No. 08/876,269, filed Jun. 16, 1997, entitled "Method and Apparatus for Dispersing Fluid Into a Material", and still pending.

BACKGROUND OF THE INVENTION

The present invention relates generally to methods and devices for dispersing a first, fluid material into a second material. It is particularly useful for evenly dispersing a first, fluid material from a first syringe into a second material within a second syringe.

The use of two syringes to mix two substances and then dispense the mixture from one of the syringes is known. U.S. Pat. No. 3,700,215 to Hardman et al. illustrates the outlet nozzles of a pair of syringes connected by a coupler. A perforated mixing tube, with perforations along the entire length thereof, is slidably mounted within the coupler so that depressing the plunger on one syringe simultaneously drives the contents of that syringe into the other syringe along with the perforated mixing tube. The plunger of the other syringe is then depressed causing the contents to be driven back into the first syringe along with the perforated mixing tube. This process is repeated a desired number of times until the substances are appropriately mixed.

U.S. Pat. No. 4,743,229 to Chu illustrates a pair of syringes coupled at their outlet nozzles. One of the syringes contains a fibrillar collagen which is injected into the second syringe which contains particulate mineral material. Excess air in the first syringe containing the particulate mineral material is expulsed through a porous piston which permits air, but not the mineral material, to pass through the piston. The collagen-mineral mixture is then dispensed from the second syringe as a collagen-based bone repair preparation.

The Chu patent shows a relatively simple system for combining two materials within the barrel of one syringe. However, the injected material is not necessarily evenly dispersed within the other material. Therefore, unless the materials are driven back and forth between the two syringes as is taught in the Hardman patent, neither good dispersion nor good mixing will likely occur. However, certain materials, such as the collagen/mineral preparation of the Chu patent, are not amenable to such flow back and forth between two syringes. Also, other preparations, such as certain insulin preparations, may be sensitive to mechanical agitation or an increase in temperature which could be created while being forced back through a relatively small orifice between the two syringes.

SUMMARY OF THE INVENTION

The present invention is directed to methods and apparatus for dispersing a fluid into a material in a simple, efficient and effective manner. The invention is adaptable for use with conventional syringes; only the fluid transfer assembly used to join the two syringes need be specially constructed.

A fluid dispersion and delivery assembly includes first and second delivery devices, typically syringes, coupled by a fluid transfer assembly. The delivery devices each include a port or access opening in fluid communication with the interior of the delivery device. The access openings are selectively fluidly coupled by the fluid transfer assembly.

The fluid transfer assembly includes a body having a central bore within which a hollow tube reciprocally passes. The hollow tube has first and second ends which are situated within the interiors of the first and second delivery devices. Openings at the ends of the tube permit fluid to be transferred from the interior of the first delivery device to the interior of the second delivery device.

The first delivery device can be prefilled with the fluid. In some situations, such as when the delivery devices are syringes and the fluid has a short shelf-life, it may be desirable to fill the first syringe with the fluid just prior to use. In such an event the fluid transfer assembly can be first mounted to the access opening of the first syringe. The plunger is depressed to cause the tube to extend from the fitting. The second end of the tube can then be placed in a reservoir or other container holding the fluid. The piston is then moved from its depressed position to its retracted position to create a partial vacuum within the second syringe; because the second end of the tube remains immersed in the fluid, the fluid is drawn up into the interior of the first syringe. At this point the second end of the tube preferably remains exposed and extends a short distance from the fitting.

The second syringe is then mounted to the fitting with the second end of the tube extending just into the interior of the second syringe. The fluid in the first syringe can be evenly dispersed into the material in the second syringe by depressing the first plunger; doing so causes the second end of the tube to pass through the material within the second syringe as the fluid is evenly dispersed into the second syringe through the opening or openings at the second end of the tube. After the fluid is dispersed into the material in the second syringe, the fluid transfer assembly can be removed from the second syringe and the combined material can be dispensed from the second syringe directly or with the aid of an additional delivery element.

The fitting is preferably a double Luer fitting to permit the fitting to be mounted to conventional syringes. If the delivery device is other than a conventional syringe, the fitting can be modified accordingly.

One of the primary advantages of the invention is that it permits a fluid, such as a hemostatic solution, to be evenly dispersed into a material, such as a flowable gel material, in a simple and convenient fashion. The use of conventional syringes as the delivery devices helps to reduce the cost of the system.

Another advantage of the invention is that only a single stroke of the first plunger is needed for even dispersion. The invention permits even dispersion even if the second material is a non-fluid, such as a dry granular material or fractured gel material, or a fluid which, because of its viscosity or other characteristics, is not suitable for passing through a small tube. In addition, heating of heat-sensitive substances or mechanical damage to agitation-sensitive substances is prevented by the elimination of multiple reciprocating plunger strokes. Also, mixing air into the combined material, which can occur when multiple reciprocations of the syringe plungers are undertaken, is reduced.

The present invention finds particular utility when used to disperse a diluent, such as a hemostatic solution, into a flowable gel material. Such materials can be used in filling tissue divots, tissue tracks, body cavities, surgical defects and the like to inhibit post-surgical spinal and other tissue adhesions. An example of such a material is disclosed in U.S. patent application Ser. No. 08/704,852 filed Aug. 27, 1996.

Other features and advantages of the invention will appear from the following description in which the preferred embodiment has been set forth in detail in conjunction with the accompanying drawings.

DESCRIPTION OF THE DRAWINGS

FIG. 4 is a top plan view of the reservoir of FIGS. 2 and 3;

FIG. 5 is a partial cross-sectional side view of a fluid dispersion and delivery assembly including the fluid-filled first syringe and fluid transfer assembly of FIG. 3 mounted to a second syringe containing a flowable gel material within its interior; and FIG. 6 illustrates the assembly of FIG. 5 after the plunger of the first syringe has been pushed to the right in the figure forcing the tube to also move to the right and causing fluid within the first syringe interior to be evenly dispersed into the material within the second syringe interior to create a combined material.

DESCRIPTION OF THE PREFERRED EMBODIMENTS

Figure 1:
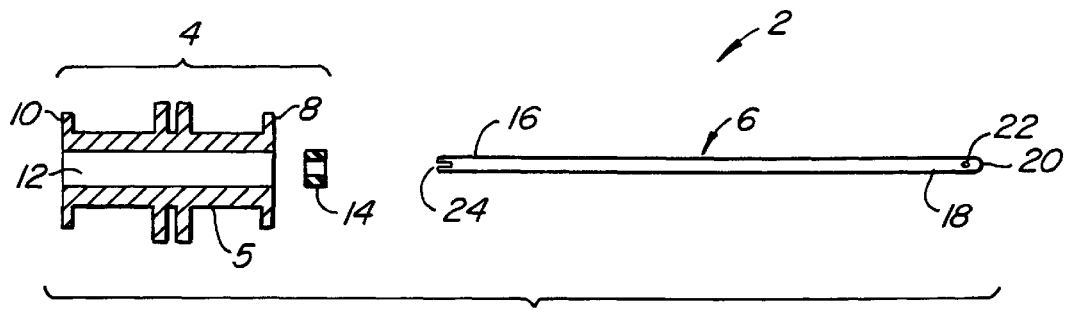
FIG. 1 is an exploded, partial cross-sectional side view of a fluid transfer assembly made according to the invention.

FIG. 1 illustrates a fluid transfer assembly 2 including a double Luer fitting 4 and a tube 6 axially slidably housed within fitting 4. Double Luer fitting 4 includes a body 5 with Luer lock elements 8, 10 at either end and a bore 12 extending along its length. An annular seal 14 is mounted over tube 6 and within bore 12 and is used to provide a sliding seal between the outer surface of tube 6 and bore 12. Seal 14 may also be, and preferably is, housed within an annular recess formed in body 5 along bore 12. Tube 6 is hollow and has first and second ends 16, 18. Second end 18 has a blunt, closed tip 20 but has four equally circumferentially-spaced exit holes 22 at second end 18. A greater or lesser number of exit holes 22 can be used. Exit holes 22 are, in this embodiment, each about 0.005–0.010" (0.13–0.25 mm) diameter for a tube 6 having an outside diameter of 0.075" (1.9 mm) and an inside diameter of 0.057" (1.4 mm). Of course the dimensions chosen will in large part be determined by the characteristics of the fluid used and flow characteristics desired. First end 16 has a radially-extending through-slot 24 providing access to the interior of the tube 6 at end 16. Slot 24 is 0.10" (2.5 mm) long and 0.0201" (0.51 mm) wide. However, for the reasons discussed below, tube 6 has holes or openings only at or near its ends 16, 18 to ensure even dispersion of a fluid during use.

Figure 2:
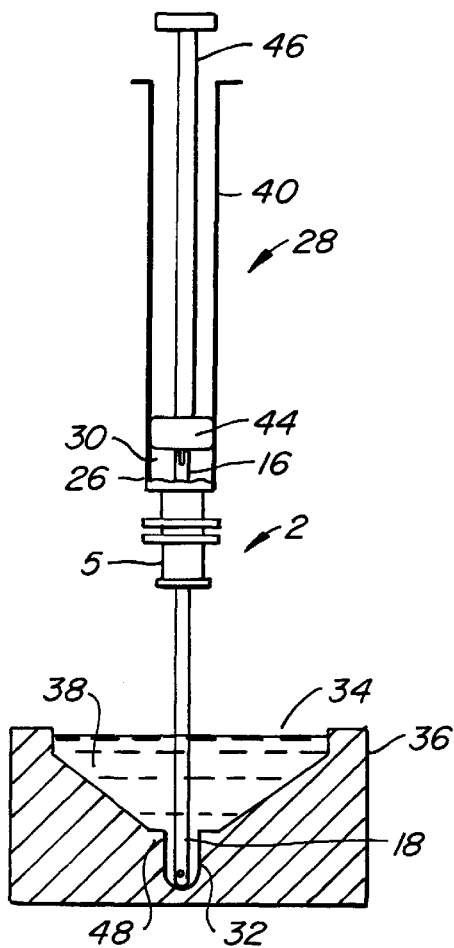
FIG. 2 is a partial cross-sectional side view of the fluid transfer assembly of FIG. 1 mounted to a first syringe with the plunger of the first syringe in a depressed position, the second end of the tube positioned in the well of a container holding a fluid.
Figure 3:
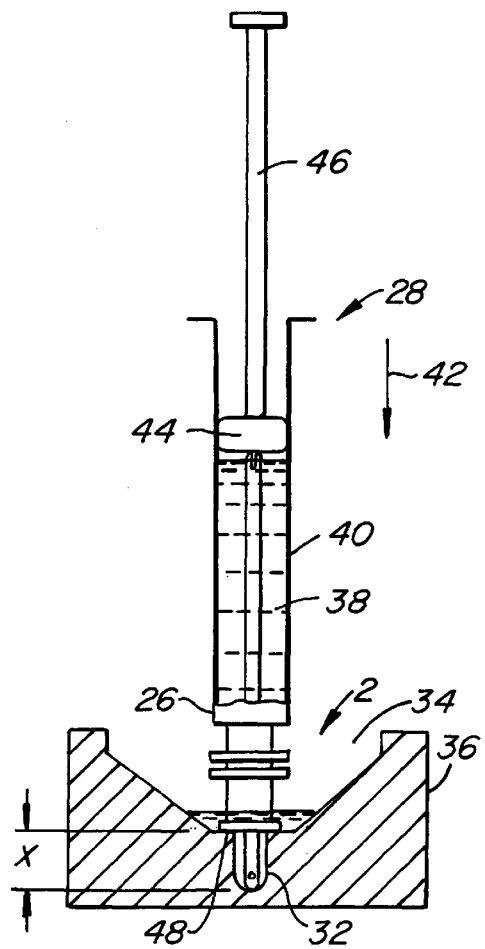
FIG. 3 illustrates the apparatus of FIG. 2 but after the barrel of the syringe has been moved downwardly towards the reservoir, the downward motion being halted by one or more stop ledges surrounding the central depression formed as part of the cavity in the reservoir, such motion causing fluid in the cavity to be drawn into the interior of the first syringe.

FIG. 2 illustrates assembly 2 assembled and mounted to the open, needle end 26 of a first syringe 28 with Luer lock element 8 engaging a Luer fitting, not shown, at end 26. As seen in FIG. 2, first end 16 extends a short distance into the interior 30 of syringe 28 so that slot 24 is in fluid communication with the interior 30 of syringe 28. To fill interior 30 with a fluid, the second end 18 of tube 6 can be positioned into a central depression 32 of a cavity 34 defined within a reservoir 36. The fluid 38 within cavity 34 can be, for example, a hemostatic solution, as well as other fluids. Hemostatic solution 38 is typically made by dissolving dried, granular component with a liquid component in reservoir 36 just prior to use. To draw fluid 38 into interior 30 of first syringe 28, the user need merely force barrel 40 of first syringe 28 downwardly in the direction of arrow 42 of FIG. 3 which causes first end 16 of tube 6 to be forced against the piston 44 of plunger 46. A partial vacuum within interior 30 of first syringe 28 created by the movement of piston 44 causes fluid 38 to pass through holes 22, along hollow tube 6 and out slot 24. As seen in FIGS. 3 and 4, the movement of barrel 40 in the direction of arrow 42 is limited by the engagement fitting 4 with four stop ledges 48 surrounding central depression 32. The position of stop ledges 48 with respect to the bottom of central depression 32 is chosen so that an appropriate length x of tube 6 remains extending from fitting 4 after first syringe 28 has been filled with fluid 38.

FIG. 5 illustrates a fluid depression and delivery assembly 49 including the combination of syringe 28 and fluid transfer assembly 2 filled with fluid 38 and mounted to a second syringe 50. Second syringe 50 includes a barrel 52 and a plunger 54 defining a second syringe interior 56 within the barrel. A material, such as a flowable gel material 58, is housed within interior 56. As seen in FIG. 5, holes 22 at second end 18 of tube 6 are located within interior 56 at one end of the interior, that is at the open needle end 60 of syringe 50 to which Luer lock element 10 has been secured. Fluid 38 is evenly dispersed into flowable gel material 58 by driving plunger 46 of first syringe 28 in the direction of arrow 62 of FIG. 6. This drives tube 6 in the direction of arrow 62 while simultaneously driving fluid 38 through holes 22 at second end 18 of tube 6 thus evenly dispersing fluid 38 into flowable material 58 to create a combined material 64. It can be appreciated that distance x of FIG. 3 is chosen so that holes 20 are properly positioned at the beginning of the stroke of plunger 46 from the position of FIG. 5 to the position of FIG. 6 to help ensure that neither too much nor too little fluid 38 is injected into second syringe 50 adjacent needle end 60. The proper selection of distance x and the use of stop ledges 48 help to ensure that fluid 38 is evenly dispersed within flowable gel material 58 within second syringe 50.

After dispersion of fluid 36 into flowable gel material 58, the fluid and material become effectively thoroughly mixed because of the affinity of flowable gel material 58 for fluid 38. This, along with the even dispersion/distribution of fluid 38 along the length of interior 56 eliminates the need for any additional mixing or agitation steps. Combined material 64 can be dispensed directly from an open, needle end 60 by simply disconnecting syringe 50 from assembly 2 and then depressing plunger 54. Alternatively, after disconnecting second syringe 50 from assembly 2, an appropriately sized and configured dispensing element could be mounted to end 60, after which plunger 54 would be depressed to dispense combined material 64.

Modification and variation can be made to the disclosed embodiment without departing from the subject of the invention as defined in the following claims. While conventional, and thus inexpensive, syringes are preferably used as the first and second delivery devices, custom syringes or other types of delivery devices could also be used. Similarly, fluid transfer assembly 2 could be mounted to first and second delivery devices using other than Luer twist-type fastener elements. The invention can be used with materials other than those discussed. For example, instead of fractured, flowable gel material 58, a liquid or a solid granular material could be used. Reservoir 36 could be made using other shaped cavities and other types of stop ledges 48. The number of stop ledges 48 can be changed from four to at least one.

Any and all patents, applications and publications referred to above are incorporated by reference.

What is claimed is:

1. A method for dispersing a first, fluid material into a second material comprising the following steps:

providing a first delivery device defining a first interior containing a first fluid material and having a first access opening;

providing a second delivery device defining a second interior containing a second material and having a second access opening;

fluidly coupling the first interior with the second interior by connecting the first access opening to the second access opening using a fluid transfer assembly, the fluid transfer assembly comprising a hollow fitting coupleable to the first and second access openings and an axially slidable tube slidably housed within the hollow fitting with a first end within the first interior and a second end within the second interior, said tube having openings therein only at or near said first and second ends;

uniformly dispersing the first material into the second material only through the opening at said second end of the tube to create a combined material;

said uniformly dispersing step comprising the step of axially driving the tube into the second delivery device so said first fluid material is introduced into the second material along the second interior in a uniform manner; and removing the fluid transfer assembly from the second delivery device.

2. The method according to claim 1 wherein the providing steps are carried out using first and second syringes as the first and second delivery devices.

3. The method according to claim 2 wherein the first delivery device providing step comprises the step of introducing a first fluid material into the first interior of the first syringe.

4. The method according to claim 3 wherein the introducing step comprises the steps of:

providing a container with the first fluid material;

positioning the tube at an intake position with a first plunger of the first syringe at a depressed position;

positioning the second end of the tube into the container so the opening at the second end is immersed within the first fluid material; and moving the plunger from the depressed position to a retracted position so said first fluid material is drawn through the tube and into the first interior.

5. The method according to claim 4 wherein the container providing step includes the step of mixing a dry component with a liquid component to create the first fluid material.

6. The method according to claim 1 wherein the first delivery device providing step comprises the step of selecting a hemostatic solution as the first material.

7. The method according to claim 1 wherein the second delivery device providing step comprises the step of selecting a flowable gel material as the second material.

8. The method according to claim 1 wherein fluidly coupling step is carried out using twist-lock fastening elements on the fluid transfer assembly.

9. The method according to claim 1 wherein the fluidly coupling step further comprises the step of selecting the tube to include an axially-extending slot at said first end.

10. The method according to claim 1 wherein the fluidly coupling step comprises the step of selecting the tube to have a plurality of radially-extending holes at said second end.

11. A method for dispersing a first, fluid material into a second material to create a combined material and dispensing the combined material comprising the following steps:

providing a first syringe defining a first interior containing a first, liquid material and having a first access opening;

providing a second syringe defining a second interior containing a second, non-liquid material and having a second access opening;

fluidly coupling the first interior with the second interior by connecting the first access opening to the second access opening using a fluid transfer assembly, the fluid transfer assembly comprising a hollow twist-lock fitting coupleable to the first and second access openings and an axially slidable tube slidably housed within the hollow fitting with a first end within the first interior and a second end within the second interior, said tube having openings therein only at or near said first and second ends;

wherein the first syringe providing step comprises the steps of:

positioning the tube at an intake position with a plunger of the first syringe at a depressed position;

positioning the second end of the tube into a container containing the first material so the opening at or near the second end is immersed within the first material;

moving the plunger from the depressed position to a retracted position so said first material is drawn through the tube and into the first interior;

uniformly dispersing the first material into the second material only through the opening at or near said second end of the tube to create a combined material;

said uniformly dispersing step comprising the step of axially driving the tube into the second syringe so said first material is introduced into the second material along the second interior in a uniform manner;

removing the fluid transfer assembly from the second syringe; and dispensing the combined material from the second syringe.

12. The method according to claim 11 further comprising the step of mixing a dry component with a liquid component to create the first material.

13. A fluid dispersion and delivery assembly comprising:

a first delivery device having a first interior capable of containing a first, fluid material, the first delivering device comprising a first access opening fluidly coupled to the first interior;

a second delivery device having a second interior capable of containing a second material, the second delivery device comprising a second access opening fluidly coupled to the second interior; and a fluid transfer assembly comprising:

a fitting removably mounting the first and second access openings to one another;

a hollow tube reciprocally housed within the fitting and having first and second ends positioned within the first and second interiors, said tube movable within the fitting between first and second positions;

said tube having openings only at or near said first and second ends; and the tube defining a fluid pathway between the openings of the first and second ends;

whereby the first material can be dispersed into the second material to create a combined material, the fluid transfer assembly can be dismounted from the second port and the combined material can be dispensed from the second delivery device.

14. The assembly according to claim 13 wherein the first delivery device comprises a syringe.

15. The assembly according to claim 13 wherein the second delivery device comprises a syringe.

16. The assembly according to claim 13 wherein the first delivery device is capable of containing a hemostatic solution as the first material.

17. The assembly according to claim 13 wherein the second delivery device is capable of containing a flowable gel material as the second material.

18. The assembly according to claim 13 wherein the opening at the second end comprises a plurality of radially-extending openings.

19. The assembly according to claim 13 wherein the fitting comprises first and second twist-lock fittings for mounting to the first and second access openings.

20. The assembly according to claim 13 wherein the elongated, hollow tube is straight.

21. A kit comprising:
  a fluid dispersion and delivery assembly comprising:
    a syringe having a first interior capable of containing a first, fluid material, the syringe comprising a first access opening fluidly coupled to the first interior;
    a delivery device having a second interior capable of containing a second material, the delivery device comprising a second access opening fluidly coupled to the second interior;
    a fluid transfer assembly comprising:
      a fitting removable mounting the first and second access openings to one another;
      a hollow tube reciprocally housed within the fitting and having first and second ends positioned within the first and second interiors, said tube movable within the fitting between first and second positions;
      said tube having openings only at or near said first and second ends; and
      the tube defining a fluid pathway between the openings of the first and second ends;
    whereby the first material can be dispersed into the second material to create a combined material, the fluid transfer assembly can be dismounted from the second port and the combined material can be dispensed from the delivery device;
  a container having an upper portion, with an access opening therein, and a lower portion, for containing the first, fluid material;

said lower portion comprising a tube stop surface for engaging the second end of said tube; and said container comprising a stop positioned to limit movement of the first delivery device towards the tube stop surface.

22. The kit according to claim 21 further comprising a flowable gel material as the second material.

23. The kit according to claim 22 further comprising a dissolvable material used to create said first fluid material.

24. A fluid dispersion and delivery assembly comprising:
  a first syringe having a first interior capable of containing a first, liquid material, the first delivering device comprising a first access opening fluidly coupled to the first interior;
  a second syringe having a second interior capable of containing a second, non-liquid material, the second delivery device comprising a second access opening fluidly coupled to the second interior; and
  a fluid transfer assembly comprising:
    a twist-lock fitting removably mounting the first and second access opening to one another;
    a hollow tube reciprocally housed within the fitting and having first and second ends positioned within the first and second interiors, said tube movable within the fitting between first and second positions;
    the fitting comprising a hollow body and a sliding seal between the hollow body and the tube;
    said tube having openings only at or near said first and second ends, said openings being radially-directed openings; and
    the tube defining a fluid pathway between the openings of the first and second ends;

whereby the first material can be dispersed into the second material to create a combined material, the fluid transfer assembly can be dismounted from the second port and the combined material can be dispensed from the second delivery device.

25. A fluid transfer assembly comprising:
  a fitting comprising a hollow body with first and second fitting elements;
  a hollow tube, having first and second ends, reciprocally housed within the hollow body, the hollow tube comprising opening s only at or near the first and second ends thereof; and
  the fitting further comprising a sliding seal between the tube and the hollow body.

26. The assembly according to claim 25 wherein the first and second fitting elements comprise first and second twist-lock fitting elements.

27. The assembly according to claim 25 wherein the hollow tube is a straight metal tube.

28. The assembly according to claim 25 wherein said opening at or near said second end comprises a plurality of radially extending openings.

29. The assembly according to claim 25 wherein said opening at or near said first end comprises a slot.

* * * * *